United States Patent [19]

Lemanski et al.

[11] 4,400,522
[45] Aug. 23, 1983

[54] PREPARATION OF MALEIC ANHYDRIDE

[75] Inventors: Michael F. Lemanski, Euclid; Gregory G. Spitnale, Bedford Hts.; Ernest C. Milberger, Solon, all of Ohio

[73] Assignee: Standard Oil Company, Cleveland, Ohio

[21] Appl. No.: 374,219

[22] Filed: May 3, 1982

Related U.S. Application Data

[62] Division of Ser. No. 210,885, Nov. 28, 1980, Pat. No. 4,360,453.

[51] Int. Cl.³ .............................................. C07D 307/60
[52] U.S. Cl. ..................................... 549/260; 549/259
[58] Field of Search ............................... 549/259, 260

[56] References Cited

U.S. PATENT DOCUMENTS

| | | | |
|---|---|---|---|
| 3,864,280 | 2/1975 | Schneider | 252/435 |
| 3,975,300 | 8/1976 | Burress | 252/435 |
| 3,985,775 | 10/1976 | Harrison | 252/435 |
| 4,002,650 | 1/1977 | Bremer et al. | 549/259 |
| 4,043,943 | 8/1977 | Schneider | 252/437 |
| 4,132,670 | 1/1979 | Katsumoto et al. | 252/437 |
| 4,147,661 | 4/1979 | Higgins et al. | 252/437 |
| 4,149,992 | 4/1979 | Mount et al. | 252/437 |
| 4,153,577 | 5/1979 | Barone | 252/437 |
| 4,158,671 | 6/1979 | Barone | 252/437 |
| 4,220,595 | 9/1980 | Dickason et al. | 252/437 |
| 4,222,945 | 9/1980 | Higgins et al. | 252/437 |
| 4,283,307 | 8/1981 | Barone et al. | 252/437 |
| 4,293,498 | 10/1981 | Lemanski et al. | 252/437 |

FOREIGN PATENT DOCUMENTS

| | | | |
|---|---|---|---|
| 3431 | 1/1979 | European Pat. Off. | |
| 1141343 | 1/1969 | United Kingdom | 252/435 |

*Primary Examiner*—Henry R. Jiles
*Assistant Examiner*—Bernard I. Dentz
*Attorney, Agent, or Firm*—Joseph G. Curatolo; Herbert D. Knudsen; Larry W. Evans

[57] ABSTRACT

The present invention provides a method for the preparation of oxidation catalysts containing mixed oxides of vanadium and phosphorus, which catalysts are particularly effective in the oxidation of n-butane, n-butenes, 1,3-butadiene or a mixture thereof with molecular oxygen or an oxygen-containing gas in the vapor phase to produce high yields of maleic anhydride with good selectivity. Vanadium phosphorus mixed oxide catalyst precursors prepared in solution in organic media are extracted from the organic media with water, with subsequent drying down to recover a precursor solid, or impregnation of a support with the aqueous solution.

10 Claims, No Drawings

PREPARATION OF MALEIC ANHYDRIDE

This is a division of application Ser. No. 210,885 filed Nov. 28, 1980 now U.S. Pat. No. 4,360,453.

BACKGROUND OF THE INVENTION

This invention relates to method for preparing catalysts useful in the production of dicarboxylic acid anhydrides by the oxidation of hydrocarbons. More particularly it is directed to the preparation of catalysts suitable for producing maleic anhydride from 4-carbon atom hydrocarbons, such as n-butane, n-butenes, 1,3-butadiene or a mixture thereof.

Catalysts containing vanadium and phosphorus oxides have been used in the oxidation of 4-carbon atom hydrocarbons, such as n-butane, n-butenes, 1,3 butadiene or mixtures thereof with molecular oxygen or oxygen-containing gas to produce maleic anhydride. A conventional method of preparing these catalysts involves dissolving a vanadium compound, a phosphorus compound, and if desired, promoter element compounds in a reducing medium under conditions which will provide vanadium in a valence state below +5 to form catalyst precursors capable of being converted to an oxide. The catalyst oxide precursor is then recovered by evaporating down the precursor-containing medium, or causing precipitation of the precursor, followed by calcining to provide active catalytic material.

The use of gaseous HC1 as a solvating and reducing agent for vanadium is disclosed in U.S. Pat. No. 4,002,650 where the vanadium and phosphorus compounds are dissolved in an aqueous solution.

European Patent Appln. No. 3,431 discloses the preparation of vanadium phosphorus mixed oxide catalysts by the dissolving and heating of a vanadium compound in an aqueous concentrated HCl solution, with subsequent addition of phosphoric acid. The solution is evaporated down to dryness and the resulting precursor solid is recontacted with water with boiling to remove inactive phase material, while the precursor solid remains suspended in the water. The solid is filtered out of the suspension, dried and calcined.

The use of gaseous HCl as a solvating and reducing agent for vanadium is also described in U.S. Pat. No. 4,043,943 where the vanadium and phosphorus components are present in solution in liquid organic medium. The catalyst precursor is recovered by evaporating or distilling down the organic medium, or, by effecting precipitation by adding inferior organic solvents for the precursor or by forming a supersaturated solution. This patent teaches that only a minor amount of water is acceptable in the medium at the time of precipitation (including evaporation or distillation).

It has been found that superior vanadium-phsophorus mixed oxide catalysts may be prepared in organic media. However, the conventional methods for recovering the catalyst precursor from organic solution, particularly by evaporation of the organic medium, poses difficulties in the commercial scale-up of catalyst production. For example, the liquid media which must be evaporated off in large quantities form flammable vapors.

SUMMARY OF THE INVENTION

It is therefore an object of the invention to provide a method of preparing vanadium and phosphorus-containing oxidation catalysts.

It is a further object of the invention to provide a method of preparing vanadium and phosphorus-containing catalysts useful for the oxidation of 4-carbon atom hydrocarbons to produce maleic anhydride, which catalysts exhibit high yields and selectivity to maleic anhydride.

It is a further object of the invention to provide a method of preparing vanadium and phosphorus-containing catalysts useful for the oxidation of 4-carbon atom hydrocarbons to produce maleic anhydride which is simplified, economical, and is capable of commercial scale-up.

It is a further object of the invention to provide a method of preparing vanadium and phosphorus-containing catalysts useful for the oxidation of 4-carbon atom hydrocarbons to produce maleic anhydride which includes improved recovery of catalyst precursors from the reaction medium.

These and other objects, together with the advantages thereof over known methods, which shall be apparent from the specification which follows, are accomplished by the invention as hereinafter described and claims.

In general the process of the present invention comprises the steps of
 (a) preparing a vanadium phosphorus mixed oxide catalyst precursor-containing organic solution;
 (b) contacting said organic solution with water;
 (c) separating the resultant aqueous phase from the organic phase;
 (d) recovering the vanadium phosphorus mixed oxide catalyst precursor;
 (e) drying the catalyst precursor;
 (f) calcining the catalyst precursor.

The catalysts prepared by the above method are particularly effective in the oxidation of 4-carbon atom hydrocarbons such as n-butane, n-butenes, 1,3 butadiene or mixtures thereof with molecular oxygen or an oxygen-containing gas in the vapor phase to product high yields of maleic anhydride with improved selectivity. Essentially all the product produced in this oxidation process is maleic anhydride, with only minor amounts of lower acids being detected.

DETAILED DESCRIPTION OF THE INVENTION

In the method for the preparation of an oxidation catalyst containing the mixed oxides of vanadium and phosphorus, a vanadium compound, particularly a pentavalent vanadium compound, is solubilized in an organic liquid medium. Suitable vanadium compounds containing pentavalent vanadium include: vanadium pentoxide or vanadium salts, such as ammonium metavanadate and vanadium oxytrihalides. Vanadium pentoxide is preferred.

The liquid medium should be a solvent for phosphoric acid and be relatively unreactive towards phosphoric acid. The liquid medium must not, however, be a solvent for the mixed oxide of vanadium and phosphorus. Suitable liquid media for use in the invention are organic compounds such as alcohols, aldehydes, ketones, ethers and mixtures of the above and are preferably anhydrous. Preferred organic liquid suitable for use in this invention are alcohols, particularly isobutanol.

After the pentavalent vanadium compound is introduced into the liquid medium, solution and reduction of the vanadium is effected, preferably by adding to the medium solubilizing and reducing agents, such as HCl or HBr gas. Preferred vanadium and phosphorus oxide catalysts for the oxidation of 4-carbon atom hydrocarbons to maleic anhydride contain vanadium in an average valence stage of about +3.5 to about +4.6. This average valence state is achieved when at least a portion of the pentavalent vanadium introduced into the liquid medium is reduced to the +4 state, preferably to an average valence state of about +4.1.

Either prior or subsequent to the reduction of the vanadium, a pentavalent phosphorus-containing compound is added to the liquid medium. Suitable phosphorus compounds containing pentavalent phosphorus include: phosphorus acid, phosphorus pentoxide, or phorphorus perhalide, such as phosphorus pentachloride. Phosphoric acid and phosphorus pentoxide are preferred. The pentavalent phosphorus-containing compound is preferably added to the reaction medium in the form of a solution of the phosphorus-containing compound in either a component of the liquid reaction medium, or in a liquid capable of yielding the phosphorus-containing compound to the liquid reaction medium. After addition of the phosphorus-containing compound to the liquid reaction medium, it is preferable to heat the liquid reaction medium with stirring, if necessary.

According to the process of the present invention, the liquid medium, which now contains the vanadium phosphorus mixed oxide catalyst precursor in solution, is contacted with water, preferably with agitation. Best results are obtained when an excess of water is used. The catalyst precursor, still in solution, is extracted into the aqueous layer (phase) which forms and which can then be separated from the organic phase by conventional multi-phase separation methods, such as centrifugation and setting.

The dissolved catalyst precursor is recovered from the aqueous solution by conventional techniques, with evaporation being preferred. Because no flammable liquids/vapors are present, evaporation is simplified, and the catalyst precursor-containing aqueous solution may be spray dried to form fluid-bed type catalyst particles. The catalyst precursor, after recovery from the aqueous solution, is dried and then calcined.

It is within the scope of this invention, to include promoter element-containing compounds in the liquid medium at a suitable point, prior to or subsequent to the reduction of the vanadium, in order that the catalyst precursor contain the promoter element. Suitable promoters include but are not limited to uranium, cobalt, molybdenum, iron, zinc, hafnium and zirconium.

Catalysts prepared by this method generally exhibit a phosphorus to vanadium ratio of about 2:1 to about 0.5:1. Preferred is a P/V ratio of about 1.2:1. The catalyst is activated by calcining it in air or an oxygen-containing gas at a temperature of 250° C. to 600° C. for a period of up to 5 hours or more. A preferred activation of the catalyst is accomplished by passing a mixture of steam and air or air alone over the catalyst at a temperature of about 300° C. to 500° C. for a period of about 1 to 5 hours.

The hydrocarbon reacted to form maleic anhydride may be n-butane, n-butenes, 1,3-butadiene, or a mixture thereof. Preferred is the use of n-butane or a mixture of hydrocarbons that are produced in refinery streams. The molecular oxygen is most conveniently added as air, but synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely and are not critical. The ratio of molecular oxygen to the hydrocarbon may range from about 2 to about 30 moles of oxygen per mole of hydrocarbon. Preferred oxygen/hydrocarbon ratios are about 4 to about 20 moles of oxygen per mole of hydrocarbon.

The reaction temperature may vary widely and is dependent upon the particular hydrocarbon and catalyst employed. Normally, temperatures of about 250° C. to about 600° C. are employed with temperatures of 350° C. to 500° C. being preferred.

The catalyst may be used alone or a support could be employed. Suitable supports include silica, alumina, silican-alumina, Alundum, silicon carbide, titania, boron phosphate, zirconia, and the like. The catalysts may be used in a fixed-bed reactor using tablets, pellets or the like, or in a fluid-bed reactor using catalysts preferably having a particle size of less than about 300 microns. The contact time may be as low as a fraction of a second or as high as 50 seconds. The reaction may be conducted at atmospheric, superatmospheric or subatmospheric pressure.

EXAMPLES 1 & 2

Catalysts of the formula $V_{1.0}P_{1.2}U_{0.2}O_x$ were prepared by the following procedure. 1008 g vanadium pentoxide and 935.5 g uranyl acetate dihydrate were added to 5.5 liters isobutanol with stirring to form a slurry. Anhydrous hydrogen chloride gas was bubbled through the liquid medium which was maintained by cooling at a temperature of about 20°±5° C. After dissolution and reduction of the vanadium (about 4 hours, at which time the temperature of the now-homogenous red-brown solution began to drop) 1303 g ortho-phosphoric acid in 2 liters isobutanol was added to the liquid medium. The liquid medium was then refluxed for 1.5 hours, acquiring a blue-green color.

One hundred milliliters of water was added to fifty milliliters of the solubilized catalyst precursor-containing liquid medium. The solubilized catalyst precursor was estimated to comprise about 30 weight percent of the liquid medium. The mixture was agitated with stirring, and was allowed to settle. The aqueous layer formed was green-colored and the organic layer was colorless. The aqueous layer was decanted and dried at 150° C. The resulting catalyst precursor solid was calcined for 10 hours at 400° C., and was ground and screened to 20–30 mesh (0.595 mm to 0.841 mm).

EXAMPLE 3

A catalyst of the formula $V_{1.0}P_{1.2}Co_{0.2}O_x$ was prepared by the procedure of Examples 1 and 2, with the exception that the 528.2 g cobaltous chloride dihydrate was substituted for the uranyl acetate dihydrate.

The catalysts prepared in Examples 1–3 were used to produce maleic anhydride from butane using a 5 cc fixed-bed reactor consisting of a 10 cm length of pyrex glass tubing having an outer diamter of about 12 millimeters. The reactor was heated with a split stainless steel block furnace. Flasks for receiving the product maleic anhydride were mounted in ice water, and tail gases were routed to a Carle Analytical Gas Chromotagraph III for analysis. Contact time was about 2 seconds and the air/hydrocarbon ratio was about 70/1. Other reaction conditions and results of the tests run are described in Table I. The results are stated in terms as follows:

Single Pass Yield = $\frac{\text{Moles of Maleic Anhydride Formed}}{\text{Moles of Butane Fed}} \times 100$ Total Conversion = $\frac{\text{Moles of Butane Reacted}}{\text{Moles of Butane Fed}} \times 100$ Selectivity = $\frac{\text{Single Pass Yield} \times 100}{\text{Total Conversion}}$ When the method of preparing catalysts containing mixed oxides of vanadium and phosphorus is employed according to the present invention, the vanadium and phosphorus-containing catalyst precursor prepared in organic liquid media can be separated from the liquid medium simply and effectively while avoiding the difficulties of evaporating off large quantities of flammable liquid/vapor. The organic liquid medium produced by the method of the present invention, after the catalyst precursor has been removed, contains little if any inorganic materials such as vanadium or phosphorus compounds, and may easily be recycled for use in the reaction again.

As can be seen from the results listed in Table I, catalysts prepared according to the method of the invention effect high yields and selectivities of 4-carbon atom hydrocarbons (such as butane) to maleic anhydride. Despite the admonitions of the prior art, warning against the presence of water at the time that the catalyst precursor which was prepared in organic liquid media is recovered, it is demonstrated by the present invention that an active vanadium phosphorus mixed oxide catalyst can be obtained when the solubilized catalyst precursor is extracted from the organic liquid with water. After extraction, the catalyst precursor can be dried, ground and screened; coated (dry) upon a support; spray dried; or the aqueous solution containing the solubilized catalyst precursor may be used to impregnate a support.

Thus it should be apparent to those skilled in the art that the subject invention accomplishes the objects set forth above. It is to be understood that the subject invention is not to be limited by the examples set forth herein. These have been provided merely to demonstrate operability, and the selection of vanadium and phosphorus-containing compounds, reducing agents, liquid media, promoter element-containing compounds if any, hydrocarbon feedstocks and reaction conditions can be determined from the total specification disclosure provided without departing from the spirit of the invention herein disclosed and described, the scope of the invention including modifications and variations that fall within the scope of the attached claims.

TABLE 1

Preparation of Maleic Anhydride from n-Butane Using $V_{1.0}P_{1.2}M_{0.2}O_x$ Catalysts*

| Example No. | Temp. °C. | % Conversion | Maleic Anhydride % Selectivity | % Yield | M-element |
|---|---|---|---|---|---|
| 1 | 403 | 51.7 | 75.2 | 38.8 | uranium |
| 2 | 427 | 76.8 | 61.0 | 46.8 | uranium |
| 3 | 458 | 93.5 | 55.4 | 51.8 | cobalt |

*x = Number of oxygens needed to satisfy the valence requirements of the other elements.

We claim:

1. A process for the production of maleic anhydride by the oxidation of n-butane, n-butene, 1,3 butadiene or a mixture thereof with molecular oxygen or oxygen-containing gas in the vapor phase at a reaction temperature of 250° C.–600° C. in the presence of a catalyst containing the mixed oxides of vanadium and phosphorus, wherein the average valence state of the vanadium is about +3.5 to about +4.6 and wherein said catalyst is prepared in an organic liquid medium, including the step of extracting the solubilized catalyst precursor from the organic liquid with water to form a solubilized catalyst precursor-containing aqueous solution.

2. The process of claim 1 wherein said catalyst is represented by the formula $$V_{1.0}P_aM_bO_x$$

wherein
M is selected from U, Co, Mo, Fe, Zn, Hf, Zr, or mixtures thereof;
wherein
a is about 0.5 to about 3,
b is zero to about 0.5
and
x is the number of oxygens needed to satisfy the valence requirements of the other elements.

3. A process for the production of maleic anhydride by the oxidation of n-butane, n-butene, 1,3 butadiene or a mixture thereof with molecular oxygen or oxygen-containing gas in the vapor phase at a reaction temperature of 250° C.–600° C. in the presence of a catalyst containing the mixed oxides of vanadium and phosphorus, wherein said catalyst is prepared by
(a) preparing a solubilized vanadium phosphorus mixed oxide catalyst precursor containing organic solution;
(b) contacting said organic solution with water;
(c) separating the resultant aqueous phase which contains said catalyst precursor from the organic phase;
(d) recovering the vanadium phosphorus mixed oxide catalyst precursor;
(e) drying the catalyst precursor;
(f) calcining the catalyst precursor.

4. The process of claim 3 wherein said vanadium phosphorus mixed oxide catalyst precursor containing solution is prepared by
(a) introducing a pentavalent vanadium-containing compound to an organic liquid medium;
(b) solubilizing and reducing the vanadium to an average valence state of about +3.5 to about +4.6;
(c) introducing a pentavalent phosphorus-containing compound to the organic liquid medium prior or subsequent to reducing the vanadium.

5. The process of claim 4 wherein the vanadium is solubilized and reduced by adding to the organic liquid medium a gas selected from hydrogen chloride, hydrogen bromide and mixtures thereof.

6. The process of claim 4 wherein the vanadium is reduced in the presence of said pentavalent phosphorus containing compound.

7. The process of claim 3 including the step of impregnating a support with said aqueous solution.

8. The process of claim 3 wherein the vanadium phosphorus mixed oxide catalyst precursor is recovered from said aqueous solution by evaporating or spray drying.

9. The process of claim 3 wherein a promoter element containing compound is introduced into the organic liquid medium prior to or subsequent to reducing the vanadium.

10. The process of claim 3 wherein said catalyst is represented by the formula $$V_{1.0}P_aM_bO_x$$

wherein

M is selected from U, Co, Mo, Fe, Zn, Hf, Zr, or mixtures thereof;

wherein a is about 0.5 to about 3, b is zero to about 0.5 and x is the number of oxygens needed to satisfy the valence requirements of the other elements.

* * * * *